United States Patent [19]

Toja

[11] Patent Number: 4,716,159
[45] Date of Patent: Dec. 29, 1987

[54] PYRIDAZINO[4,3-C]-ISOQUINOLINES HAVING ANTI-ANXIETY ACTIVITY

[75] Inventor: Emilio Toja, Milan, Italy

[73] Assignee: Gruppo Lepetit, S.p.A., Gerenzano, Italy

[21] Appl. No.: 891,815

[22] Filed: Jul. 30, 1986

Related U.S. Application Data

[63] Continuation of Ser. No. 626,354, Jun. 29, 1984, abandoned.

[30] Foreign Application Priority Data

Jul. 12, 1983 [IT] Italy ................................ 22013 A/83

[51] Int. Cl.⁴ ..................... A61K 31/50; C07D 471/04
[52] U.S. Cl. .................................... 514/210; 514/211; 514/222; 514/227; 514/248; 540/544; 540/553; 540/609; 544/115; 544/234; 544/239
[58] Field of Search ............... 544/234, 115, 106, 239; 514/248, 227, 211, 222; 546/81, 82, 88; 540/544, 553, 609

[56] References Cited

PUBLICATIONS

Toja, E. et al., Tetrahedron Lett, 31, pp. 2921-2924 (1979).

Primary Examiner—Donald G. Daus
Assistant Examiner—Mark W. Noel
Attorney, Agent, or Firm—Stephen L. Nesbitt

[57] ABSTRACT

The present invention is directed to pyridazino[4,3-c]isoquinolines of Formula I

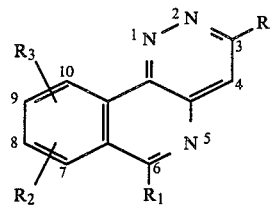

wherein R represents methyl, phenyl or substituted phenyl groups, $R_1$ represents inter alia amino or substituted amino, alkoxy or cycloalkoxy groups, having pharmacological activity, to process for preparing them and to the pharmaceutical compositions containing them. The compounds of the invention possess anti-anxiety activity.

7 Claims, No Drawings

PYRIDAZINO[4,3-c]-ISOQUINOLINES HAVING ANTI-ANXIETY ACTIVITY

This is a continuation of application Ser. No. 626,354 filed June 29, 1984 now abandoned.

The present invention is directed to new pyridazino[4,3-c]isoquinoline derivatives, to the process for their preparation and to the pharmaceutical compositions containing them. The new pyridazino[4,3-c]isoquinoline derivatives of the present invention are represented by the following Formula I

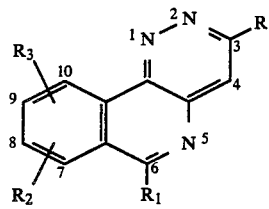

wherein R represents methyl, phenyl or substituted phenyl wherein the phenyl ring is substituted with from 1 to 3 substituents selected from $(C_1-C_4)$alkyl, $(C_1-C_4)$alkoxy, halogen, hydroxy, phenyl, amino and trifluoromethyl; $R_1$ represents hydrogen, chloro, a group of formula $-NR_4R_5$ wherein $R_4$ and $R_5$, each independently, represent hydrogen, $(C_1-C_4)$alkyl, $(C_2-C_4)$alkenyl, $(C_2-C_5)$alkanoyloxymethyl, $(C_1-C_4)$alkoxycarbonyl, $(C_1-C_4)$ alkyl substituted with one or two groups independently selected from hydroxy, $(C_1-C_4)$alkoxy, halogen, carboxy, cyano and aminocarbonyl; phenyl-$(C_1-C_4)$alkyl or substituted phenyl-$(C_1-C_4)$alkyl wherein the alkyl portion may be substituted with one or two groups selected from hydroxy, $(C_1-C_4)$alkoxy, halogen, carboxy, $(C_1-C_4)$alkoxycarbonyl, and $(C_2-C_4)$alkanoyloxymethyl, and the phenyl portion may be substituted as defined, above, or $R_4$ and $R_5$ taken together with the adjacent nitrogen atom represent a saturated 4, 5, 6, or 7-membered heterocyclic ring which may contain a further heteroatom selected from nitrogen, oxygen, and sulfur and optionally bear one or two substituents independently selected from $(C_1-C_4)$alkyl, phenyl, hydroxy, and carbo$(C_1-C_4)$alkoxy, or $R_1$ represents an alkoxy or cycloalkoxy group of Formula $-OR_6$ wherein $R_6$ stands for a $(C_1-C_6)$alkyl substituted with one or two groups independently selected from hydroxy, amino, mono- or di-$(C_1-C_4)$alkylamino, $(C_1-C_4)$alkoxy, halogen, oxo, carboxy, aminocarbonyl, mono- or di-$(C_1-C_4)$alkylaminocarbonyl, and $(C_1-C_4)$alkoxycarbonyl, or $R_6$ is a $(C_5-C_8)$cycloalkyl group optionally substituted with at least one substituent selected from hydroxy and $(C_1-C_4)$alkoxy, $R_2$ and $R_3$ independently represent hydrogen, halogen, $(C_1-C_4)$alkyl or $(C_1-C_4)$alkoxy; and the pharmaceutically acceptable acid addition salts thereof.

In the present specification and claims the term "substituted phenyl" indicates a phenyl ring which is substituted with from 1 to 3 substituents selected from $(C_1-C_4)$alkyl, $(C_1-C_4)$alkoxy, halogen, hydroxy, phenyl, amino and trifluoromethyl.

The term "$(C_1-C_4)$alkyl", as such or in a group which contains it, refers to straight or branched hydrocarbon group of one to four carbon atoms, such as methyl, ethyl, propyl, 1-methylethyl, butyl, 1-methylpropyl, and 1,1-dimethylethyl.

The term "$(C_1-C_4)$alkoxy", as such or in a group which contains it, refers to a straight or branched alkoxy group of one to four carbon atoms such as: methoxy, ethoxy, propoxy, butoxy, 1-methyl-1-ethoxy, 1,2-dimethyl-1-ethoxy, and 1,1-dimethyl-1-ethoxy. The term "$(C_2-C_4)$alkenyl" refers to alkenyl groups of 2 to 4 atoms such as: vinyl, 1-propenyl, 2-propenyl, butenyl, 2-butenyl, 2-methyl-1-propenyl and the like.

The term "halogen" identifies a halogen atom selected from chlorine, bromine, fluorine, and iodine. The term "mono-" or "di-" "$(C_1-C_4)$alkylamino" refers to amino substituents respectively mono- or di- substituted with a $(C_1-C_4)$alkyl group as defined above.

Representative examples of "$(C_5-C_8)$ cycloalkyl groups" are: cyclopentyl, cyclohexyl, cycloheptyl, and cyclooctyl.

Representative examples of "saturated 4, 5, 6, or 7 membered heterocyclic rings" as defined in the present invention are: oxazolidinyl, isoxazolidinyl, azetidinyl, pyrrolidinyl, piperidinyl, pyrazolidinyl, pyrazinidyl, pyrimidinyl, pyridazinidyl, morpholinyl, imidazolidinyl, piperazinyl, triazolidinyl, perhydroazepinyl, perhydrodiazepinyl and the like.

Examples of "$(C_2-C_6)$alkanoyloxymethyl" are: acetyloxymethyl, propionylcxvmethyl, butyryloxymethyl, 2-methylpropanoyloxymethyl 2,2-dimethylpropanoyloxymethyl, (i.e., pivaloyl), pentanoyloxymethyl, hexanoyloxymethyl, 3-methylpentanoyloxymethyl and the like.

Representative acid addition salts of the compounds of Formula I include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and like acids. The transformation of the free amino compounds of the invention into the corresponding acid addition salts, and the reverse, i.e. the transformation of an acid addition salt of a compound of the invention into the non-salt or free amino form, are within the ordinary technical skill and are encompassed by the present invention. In view of the similarity of the properties of the compound of Formula I and their salts, what is said in the present application when dealing with the biological activities of the compounds of Formula I applies also to their pharmaceutically acceptable salts, and vice versa.

A preferred group of compounds of the invention includes those compounds of Formula I wherein R is methyl, phenyl or substituted phenyl, $R_1$ is group of Formula $-NR_4R_5$ wherein $R_4$ and $R_5$ independently represent hydrogen, $(C_1-C_4)$alkyl, and $(C_1-C_4)$alkyl substituted with one group selected from $(C_1-C_4)$alkoxy and hydroxy or $R_4$ and $R_5$ taken together with the adjacent nitrogen atom represent a saturated heterocyclic group selected from azetidinyl, pyrrolydinyl, piperidinyl, pyrazolidinyl, pyrazinidyl, pyrimidinyl, pyridazinidyl, morpholinyl, imidazolidinyl and piperazinyl, $R_2$ and $R_3$ independently represent hydrogen or halogen atoms. The process of the invention is outlined in the following Scheme:

SCHEME I

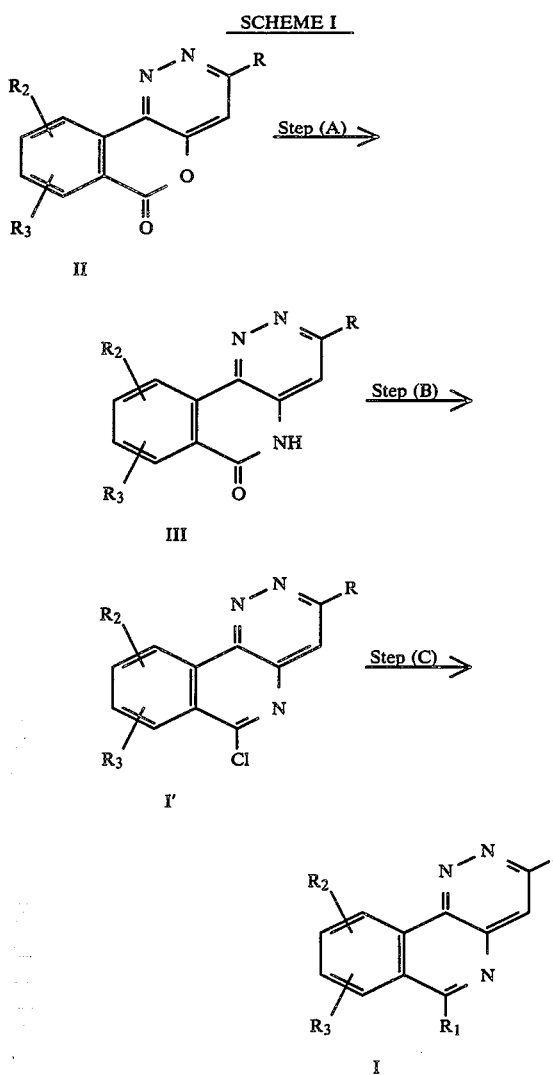

The first step of reaction procedure is the opening of the lactone bond of the compound of Formula II and its cyclization to give the lactam compound of Formula III. More particularly, this reaction step comprises reacting a 6H-[2]benzopyrano-[4,3-c]pyridazin-6-one of Formula II, wherein R, $R_2$ and $R_3$ are as defined above, with a molar excess of ammonia or an ammonium salt capable of readily giving ammonia under the reaction conditions. Examples of such ammonium salts are ammonium acetate and the other ammonium salts of weak acids. The reaction may be carried out in autoclave, without the need of adding an inert solvent, or in the presence of a polar aprotic solvent such a lower alkanol, e.g., methanol and ethanol, or preferably in the presence of an organic acid such as acetic acid. When a solvent is used, generally the reaction mixture is heated to the reflux temperature to accelerate the reaction, even if it may take place also at room temperature. The pyridazino-[4,3c]isoquinolin-6(5H)-one derivative of Formula III so obtained is recovered by evaporating the solvent under reduced pressure and/or by collecting the precipitate by filtration and washing with water. This intermediate may be purified by crystallization, if desired. In general it can be used as such in the subsequent reaction step, without crystallizing.

The next step, Step B, is characterized by the substitution of the oxo function in position 6 with a chlorine atom. To do this the pyridazino[4,3-c]isoquinolin-6-(5H)-one of Formula III is reacted with a chlorinating agent such as $PCl_5$ or $POCl_3$. This reaction may be conducted by using a molar excess of $POCl_3$ as the reaction solvent or by operating in the presence of a chlorinated organic solvent, such as carbon tetrachloride, methylene dichloride and the like, preferably heating to the reflux temperature of the reaction mixture. The reaction course can be monitored by means of TLC. When the reaction is completed, the chlorinating agent excess is eliminated according to usual techniques. The obtained product is then purified by crystallization.

The chlorine atom in position 6 of the pyridazino[4,3-c]isoquinolin-6-(5H)-one derivative of Formula I may be substituted with an amine of Formula $-NR_4R_5$ or an alkoxy or cycloalkoxy group of Formula $-OR_6$, wherein $R_4$, $R_5$ and $R_6$ are as defined above. More particularly, this substitution step is preferably conducted by reacting, preferably at the reflux temperature, the selected 6-chloro-pyridazino[4,3-c]isoquinoline with at least a molar amount of the amine of Formula $HNR_4R_5$ or alkoxide or cycloalkoxide of Formula $MeOR_6$, wherein the substituents are as above defined and Me represents an alkali metal. When the amine of Formula $HNR_4R_5$ is used, the addition of an organic solvent may not be necessary since the excess of the amine itself may act as the reaction medium. On the contrary, when the reagent is an alkoxide of Formula $MeOR_6$ the presence of an inert organic solvent is necessary. Representative examples of inert organic solvent which may be used in this reaction-step are lower alkanols of formula $R_6OH$, (i.e. an excess of the alcohol corresponding to the alkoxide being employed) glycol ethers, dioxane, tetrahydrofuran, and the like. When a pyridazino[4,3-c]isoquinoline compound of Formula I is obtained wherein at least one of $R_4$ and $R_5$ is a hydroxy($C_1$-$C_4$)alkyl group, it may be transformed into the corresponding halo ($C_1$-$C_4$)alkyl derivative by means of the known per se halogenating reactions. These halo($C_1$-$C_4$)alkyl derivatives of Formula I may then be transformed into the corresponding compounds of Formula I wherein $R_4$ and/or $R_5$ represents a ($C_1$-$C_4$)alkoxy($C_1$-$C_4$)alkyl group.

The pyridazino[4,3-c]isoquinolines of Formula I wherein $R_1$ is hydrogen are conveniently obtained by catalytically hydrogenating the corresponding compounds wherein R is chloro, preferably using 10% palladium on carbon in the presence of about a stoichiometric amount of magnesium oxide over the starting 6-chloro derivative, at room temperature and ambient pressure. The 5,6-dihydro-pyridazino[4,3-c]isoquinoline so obtained is then selectively dehydrogenated, preferably by using iodine in the presence of potassium acetate or other equivalent strong base in a polar aprotic inert solvent such as ethanol.

The starting materials of Formula II can be prepared as described in the literature (see E. Toja et al., Tetrahedron Letters, 1979, 31, pages 2921-2924). More particularly, a general procedure for preparing these starting materials includes a base-catalyzed rearrangement of a hydrazone of Formula IV

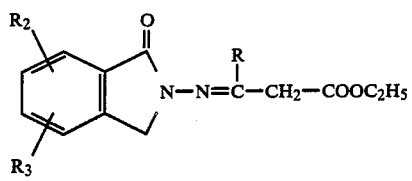

to give a 3-aryl-4-(1H)-pyridazinone of Formula V

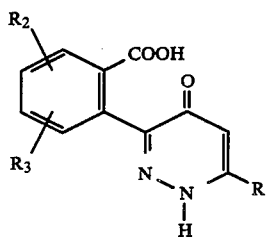

which is then treated with a condensating agent to give the 6H-[2]-benzopyrano[4,3-c]pyridazin-6-one derivative of Formula II.

The hydrazones of Formula IV are in turn prepared by condensing a N-aminophthalimidine derivative of Formula VI

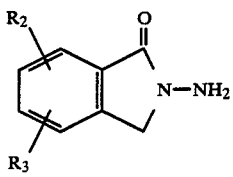

with a benzylacetic acid ethyl ester of Formula VII

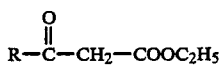

according to known techniques (see E. Toja, Tetrahedron Letters, No. 2, pages 111-114).

The anti-anxiety activity of the compounds of the present invention was first detected by submitting some representative compounds to the benzodiazepine receptor test. It has been known in fact that specific binding sites exist for benzodiazepines in the central nervous system which act in mediating the anxiolytic properties of benzodiazepines and it was demonstrated (see for instance S. Lippa et al., Pharmacol. Biochem. & Behaviour, Vol. 9, 853-856 (1978) and H. Möhler and T. Okada, Brit. J. Psychiat., 133, 261-68 (1978)) that the ability of a substance to displace $^3$H-Diazepam from its specific rat brain receptors is significantly correlated with its anxiolytic properties. Our experiments were carried out by following the method described by H. Möler and T. Okada in Life Sciences, Vol. 20, 2101-2110 (1977).

The results obtained in these tests with some representative compounds of the present invention are summarized in the following Table I:

TABLE I

| Compound of Example | Inhibition %* | $K_i$ |
|---|---|---|
| 1 | −36% | |
| 2 | | $2,84 \times 10^{-8}$ |

TABLE I-continued

| Compound of Example | Inhibition %* | $K_i$ |
|---|---|---|
| 3 | | $6,52 \times 10^{-8}$ |
| 4 | | $1,36 \times 10^{-7}$ |
| 5 | | $1,14 \times 10^{-8}$ |
| 6 | | $1,52 \times 10^{-7}$ |
| 9 | | $1,48 \times 10^{-6}$ |
| 10 | | $1,9 \times 10^{-6}$ |
| 13 | | $6,33 \times 10^{-8}$ |
| 14 | | $2,21 \times 10^{-7}$ |
| 15 | | $1,18 \times 10^{-6}$ |
| 16 | −69% | |
| 17 | | $1,3 \times 10^{-7}$ |
| 18 | | $1,87 \times 10^{-8}$ |
| 19 | −70% | |
| 20 | −76% | |
| 21 | −39% | |
| 22 | −61% | |
| 24 | −47% | |
| 27 | −63% | |
| 32 | | $2,45 \times 10^{-7}$ |

*Percent of inhibition of the $^3$H diazepam binding at a concentration of the test compound of 3,6 μM.

The ability of the compounds of the present invention to increase punished responding in animals in a conflict situation, a procedure with high validity for predicting the anxiolytic effect of drugs, was assessed by testing these compounds in rats according to the method described by J. R. Vogel, B. Beer, D. E. Clody in Psycopharmacologia 21, 1-7, (1971) as modified by A. S. Lippa et al., in "Anxiolytics, Industrial Pharmacology", Vol. 3, Futura Publishing, 1979, pages 41-81.

Briefly, rats are deprived of water for 48 hours and deprived of food for 20 hours prior to testing. Sixty minutes after administration of the test compound each rat is placed in an specially equipped cage. A glucose solution is available from a tap located in the rear of the cage. A constant pulsating shocking current is connected between the grid floor and the tap. Each rat is allowed 20 seconds of non-shocked drinking, then cycles of 5 seconds shock-off and 5 seconds shock-on began. During the shock-on period each lick on the top is accompanied by shock. The number of shocks received by each animal is recorded and minimal effective doses are determined.

The following table lists the minimal effective doses (MED) which significantly increased the number of shocks in treated animals in comparison with controls for some representative compounds of the invention.

TABLE

| Compound of Example No. | MED (Mg/Kg, i.p.) |
|---|---|
| 2 | 10 |
| 3 | 10 |
| 4 | 30 |
| 5 | 5 |
| 6 | 15 |
| 13 | 10 |
| 14 | 30 |
| 15 | 10 |
| 17 | 30 |
| 18 | 20 |
| 19 | 10 |
| 20 | 30 |
| 32 | 20 |

Representative compounds of the invention proved to be practically devoid of anticonvulsant activity in pentylenetetrazole and bicuculline tests in mice at doses up to 100 mg/kg. The antipentylenetetrazole assay in mice have been carried out by essentially following the methodology described by Berger in J. Pharm. Exptl. Ther. 104, 468, (1952). A fatal dose of pentylenetetrazole (140 mg/kg, s.c.) was administered to groups of ten mice each, treated, 30 minutes before the administration of the convulsant agent, with a selected dose of the test compound. One group of animals, the "control" group, did not receive the test compound but only the convulsant agent. The compounds of Examples 3, 4, 5 and 6 failed to prevent tonic extensor seizures at the dose of 100 mg/kg, (highest dose tested) while the compounds of Examples 2, 13, 14, 15, 17, 18, 19, 20, and 32 were uneffective at the dose of 50 mg/kg (highest dose tested).

Diazepam in the same experiment has an $ED_{50}$ (dose which prevents tonic extension seizures in 50% of the treated animals) of 0.2 mg/kg, i.p. In a similar way representative compounds of the invention were submitted to the anti-bicuculline test, which is another assay system for detecting an anticonvulsant activity. The experiments were conducted essentially following the methodology described by P. De La Mora et R. Tapia in Biochem. Pharmac. 22, 2635–2639 (1973). A dose of bicuculline (2 mg/kg, s.c.) was administered to groups of ten mice each which had been given a fixed dose of the text compound 30 minutes before treatment. One group of animals, the control group, did not receive the test compound but only the convulsant agent and the vehicle. In this test, the compounds of Examples 2, 13, 14, 15, 17, 18, 19, 20, and 32, failed to prevent seizures at the dose of 100 mg/kg, i.p. (highest dose tested) while the compounds of Examples 3, 4, 5, and 6 were uneffective at the dose of 50 mg/kg, i.p. (highest dose tested). In the same experiment Diazepam had an $ED_{50}$ (dose which prevents tonic extensor seizures in 50% of the treated animals) of 0.18 mg/kg, i.p. One aspect of the compounds of the present invention is therefore that their "antianxiety" activity in experimental models appears to be dissociated from a possible "anticonvulsant" activity. As reported above, the fact that representative compounds of the invention proved to possess "anxiolytic" features in experimental models known to be predictive of an anxiolytic pharmacological activity (see the results of the benzodiazepine receptor and rat conflict tests, above) and proved simultaneously to be devoid of anticonvulsant activity (see the results of the antipentylenetetrazole and anti-bicuculline tests, above) at doses highly superior to the effective doses as "antianxiety" substances is rather uncommon. The significance of this fact has not yet been completely clarified since it was first described only recently for two quinoline derivatives (see G. Le Fur et al., Life Sci., 28, 1439–1448 (1981)). In view of the above it seems to be possible, however, to define the present compounds as "pure anticonflict" compounds as opposed to "common" antianxiety compounds (diazepam included) which are effective both in animal anticonflict and anticonvulsant tests. The favourable pharmacological properties of the compounds of the present invention are accompanied by a generally low toxicity, as in fact the acute toxicity of the compounds of the present invention is in general from 200 to more than 600 mg/kg, i.p. In view of the above, the use of the compounds of the present invention as anticonvulsant and antianxiety agents is a further specific object of the present invention. With the term "use" it is intended to refer to all industrially applicable aspects and acts of said use, including the embodiment of the novel compounds into pharmaceutical compositions.

Suitable pharmaceutical compositions contain the novel compounds in admixture or conjunction with organic or inorganic, solid liquid pharmaceutical excipients and may be employed for enteral and parenteral administration. Suitable excipients are substances that do not react with the new compounds such as for instance, water, gelatin, lactose, starches, magnesium stearate, talcum, vegetable oils, benzyl alcohol, polyalkyleneglycols, or other known medicinal excipients. The new compounds may be administered by various routes: orally, intramuscularly or intravenously, for example, the oral route being the most preferred one. For oral administration the substances are compounded in such forms, as tablets, dispersible powders, capsules, granules, syrups, elixirs and solutions. For intravenous or intramuscular administration the active ingredients are embodied into injectable dosage forms. Such compositions are formulated as known in the art. The dosage regimen for the compounds of the present invention for an anti-anxiety treatment will depend upon a variety of factors including the particular compound used, the route of administration, and the type of treatment. Good results can be obtained by administering the compounds of the present invention at a daily dosage range comprised between about 0.1 and about 2.0 g preferably in divided doses. It is however clear that a daily dosage beyond the above indicated range may also be employed depending on the individual conditions of the subject to be treated. Accordingly, the present invention provides a therapeutic composition containing from about 5 to about 500 mg and preferably between 25 and 250 mg of one of the compounds of the invention as the active ingredient together with a pharmaceutically acceptable carrier.

Illustrative pharmaceutical formulations which may be employed in practicing the present invention are:

| Preparation of a capsule | | |
|---|---|---|
| 3-Phenyl-6-pyrrolidinyl)pyridazino-[4,3-c]isoquinoline | | 200 mg |
| Sucrose | | 35 mg |
| Polyvinylpyrrolidone | | 5 mg |
| Sodium Dioctylsulfosuccinate | | 1,8 mg |
| Magnesium Stearate | | 10 mg |
| Corn Starch | q.s. | 300 mg |
| Preparation of a tablet | | |
| 3-Phenyl-6-(1-pyrrolidinyl)pyridazino-[4,3-c]isoquinoline | | 150 mg |
| Sucrose | | 300 mg |
| Polyvinylpyrrolidone | | 5 mg |
| Sodium Dioctylsulfosuccinate | | 1,4 mg |
| Magnesium Stearate | | 8 mg |
| Corn Starch | q.s. | 250 mg |

The following Examples further describe the process of the invention as well as some representative compounds of the invention and should not be construed as limiting the overall scope of the present invention.

Preparation of the starting materials (A) 3-Phenyl-6H-[2]benzopyrano-[4,3-c]pyridazine-6-one which is the starting material used in Example 1 is described in Tetrahedron Letters, No. 31, pages 2921–24 (1979). 3-(4-Methoxyphenyl)-6H-[2]benzopyrano -4,3-c]/pyridazin-6-one which is the starting material used in Example 11 has been prepared according to the following procedure:

Ethanol (1500 ml) and 3-]( 2,3-dihydro-1-oxo-1H-2-isoindolyl)imino ]-3-(4-methoxyphenyl)propanoic acid ethyl ester (M.p. 89°–90° C.) (105,7 g, 0,3 mol) are heated to about 60° C. in a 3 litre flask, under nitrogen stream and anhydrous conditions. When a solution is obtained, sodium ethylate (24 g, 0,33 mol) is added thereto, portionwise. Heating at 60° C. is continued for about 1 hour until when a red precipitate forms. The ethanolic phase is evaporated under reduced pressure and the residue is poured into a mixture of 3 litres of water and 300 ml of 2N aqueous sodium hydroxide, wherein oxygen is rapidly bubbled. This water suspension is kept to about 40° C. by bubbling in warm steam. After about 4 hours the cloudy yellow solution is extracted with ethyl ether (4×500 ml). The aqueous layer is treated with carbon, the pH is adjusted to about 3 with concentrated hydrochloric acid (80 ml) and 10% hydrochloric acid (25 ml). The precipitate which forms is recovered by filtration oven dried over $P_2O_5$, yielding 2-[4-hydroxy-6-(6-methoxyphenyl)-3-pyridazinyl]-benzoic acid M.p. 224°–227° C. (from methanol 72.1 g)( Yield 74%).

(B) Acetic acid anhydride (100 ml), 2-[4-hydroxy-6-(4-methoxyphenyl)-3-pyridaziny]benzoic acid (11 g, 0.0342 mol) and toluene (100 ml) are reacted in a 250 ml flask; oil bath about 130° C. When the reaction is completed, the mixture toluene/acetic acid is distilled off at 96–108° C. (about 100 ml/1.5 hours). The acetic acid anhydride is eliminated under vacuum, the residue is taken up with methylene chloride (250 ml), washed with 5% aqueous sodium bicarbonate and then with water up to neutrality. THe organic layer is oven dried, and concentrated to dryness to give 3-(4-methoxyphenyl)-6H-[2]-benzopyrano[4,3-c]pyridazin-6-one 230°–231° C. (9,8 g; Yield 92%).

3-(4-Chlorophenyl)-6H-[2]benzopyrano-[4,3-c pyridazin-6-one (M.p. 273°–275° C.) which is the starting material in the preparation described in Example 12 has been prepared according to the foregoing procedure, but starting from 3-(4-chlorophenyl)-3-[(2,3-dihydro-1-oxo-1H-2-isoindolyl)imin-o/propanoic acid ethyl ester and having 2-[6-(4-chlorophenyl)-4-hydroxy-3-pyridazinyl-]benzoic, acid monohydrate (M.p. 270° C.) as the intermediate.

Analogously 3-methyl-6H-[2]benzopyrano[4,3-c]pyridazin-6-one (m.p. >350° C.) which is the starting material for the compound of Example 32 has been prepared according to the foregoing procedure but starting from 3-methyl-3-(2,3-dihydro-1-oxo-1H-2-isoindolyl)imino]propanoic acid ethyl ester and having 2-[6-methyl-4-hydroxy-3-pyridazinyl]benzoic acid (214–216 dec.) as the intermediate.

The starting materials of these last preparations are in turn prepared according to E. Toja et al., Tetrahedron Letters, 1976, page 111.

EXAMPLE 1

6-Chloro-3-phenyl-pyridazino-[4,3-c]-isoquinoline.

(A)3-Phenyl-6H-[2]benzopyrano-]4,3-c]pyridazin-6-one (11 g, 0.04 mol) and ammonium acetate (110 g) are put in an autoclave and heated to 190° C. for 9 hours. When the reaction is completed, the mixture is cooled and the solid mass is washed and disaggregated with water. The solid is separated by filtration and dried obtaining 3-phenyl-pyridazino [4,3-c]isoquinolin-6-(5H)-one in a 97% yield. M.p. 340°–342° C.

(B) Phosphorus oxychloride (760 ml), 3-phenyl-pyridazino[4,3-c]isoquinolin-6(5H)-one (74 g, 0.27 mol) and phosphorus pentachloride (58 g, 0.278 mol) in a 2 litre flask are heated to reflux temperature with stirring. Heating is continued for about 3.5 hours, then a solution is obtained which is evaporated under reduced pressure to eliminate the phosphorus oxychloride excess. The solid is taken up with benzene and then evaporated to dryness in order to eliminate all the unreacted phosphorus oxychloride. Then the reaction mass is taken up with methylene chloride (1500 ml) and washed with 10% aqueous ammonium acetate (two times; first with 800 ml and then with 400 ml), and subsequently with water up to neutrality. The methylene chloride phase is dried on magnesium sulfate and the solvent is evaporated under reduced pressure. The solid residue is disaggregated and washed with methylene chloride (300 ml) and filtered, yielding 6-chloro-3-phenyl-pyridazino-[4,3-c]isoquinoline (63 g). By concentrating the mother liquors to dryness and crystallizing the obtained solid from acetone, 11 g of the same product is obtained. These two crops of 6-chloro 3-phenylpyridazino[4,3-c]isoquinoline derivatives are pooled and recrystallized from acetone, with a 90% overall yield. The product has a melting point of 177°–178° C.

EXAMPLE 2

3-Phenyl-N,N-dimethyl-pyridazino-[4,3-c]-isoquinolin-6-amine.

Dimethylamine (6 g), 6-chloro-3-phenyl-pyridazino-[4,3-c]isoquinoline (5.83 g, 0.02 mol) and dimetoxyethane (120 ml) are heated at 120° C. for about 8 hours in a bomb. Then the reaction mixture is concentrated to dryness under reduced pressure, the residue is disaggregated with water (200 ml) and the solid recovered by filtration is dried, yielding 5.8 g of a crude product which is crystallized from acetone to give 3.2 g of the product of the title. M.p. 134°–136° C. A further crop of about 1,7 g is obtained by purifying the residue of the concentration of the mothers liquors by means of a silica gel column chromatography which uses chloroform as the eluent. Overall yield 4,9 g (81,5%).

EXAMPLES 3–4

The following compounds are obtained by following the procedure of the foregoing example but substituting dimethylamine with the selected amine derivative.

EXAMPLE 3

N-ethyl-3-phenyl-N-methylpyridazino-[4,3-c]-isoquinolin-6-amine.

Yield 71,5% M.p. 130°–133° C. (from ethyl acetate)

EXAMPLE 4

1-[(3-Phenyl-pyridazino[4,3-c]isoquinolin-6-yl)methylamino]-2-propanol.

Yield 77%; M.p. 161°–162° C. (from ethanol).

EXAMPLE 5

3-phenyl-6-(1-pyrrolidinyl)pyridazino-[4,3-c]isoquinoline.

3-Phenyl-pyridazino-[4,3-c]isoquinoline (5.83 g, 0.02 mol) and dimethoxyethane (100 ml) are heated to reflux temperature with stirring in a 250 ml flask. Pyrrolidine (3.1 g, 0.044 mol) is added to the obtained solution and heating is continued for further 2 hours. When the reaction is completed, the reaction mixture is concentrated to dryness under reduced pressure and the residue is taken up with water (200 ml), a solid is recovered by filtrating the obtained suspension which is dried yielding 6.1 g of a crude 3-phenyl-6-(1-pyrrolidinyl)-pyridazino[4,3-c]isoquinoline. Crystallization from ethyl acetate gives 5.6 g of the pure product of the title. (Yield 85%) M.p. 174°–176° C.

EXAMPLES 6–8

By essentially following the procedure of the foregoing examples but using the selected amine instead of pyrrolidine, the following compounds are obtained:

EXAMPLE 6

3-Phenyl-6-(4-morpholinyl)pyridazino[4,3-c]-isoquinoline.

Yield 82%; M.p. 214°–216° C. (from ethyl acetate)

EXAMPLE 7

3-Phenyl-(4-phenyl-1-piperazinyl)pyridazino-[4,3-c]isoquinoline. Yield 78%; M.p. 204°–206° C. (from benzene)

EXAMPLE 8

3-Phenyl-N-(phenylmethyl)pyridazino-[4,3-c]-isoquinolin-6-amine.

Yield 96%; M.p. 207°–209° C. (from ethyl ether)

EXAMPLE 9

6-Ethoxy-3-phenyl-pyridazino [4,3-c]isoquinoline.

A solution of sodium ethoxide is prepared by reacting ethanol (50 ml) and sodium metal (0.5 g) in a 500 ml flask under nitrogen stream. The mixture is gently warmed to about 30° C. and 6-chloro-3-phenyl-pyridazino[4,3-c]isoquinoline (5.83 g, 0.02 mol) is slowly added thereto. This mixture is slowly heated to about 80° C. and kept to this temperature for about 1 hour, the reaction course is monitored by TLC as usual and, when the reaction is completed, the reaction mass is concentrated to dryness under reduced pressure, the residue is taken up with a little amount of water, the solid is recovered by filtration and dried under vacuum. The crude product which residuates is crystallized from acetone giving 6-ethoxy-3-phenyl-pyridazino-[4,3-c]isoquinoline. (Yield 92%).

M.p. 155°–156° C.

EXAMPLE 10

3-Phenyl-6-(1-methylethoxy)pyridazino-[4,3isoquinoline. This compound is obtained by essentially following the procedure of the foregoing example but using isopropanol instead of ethanol and heating the reaction mixture at about 60° C. for about 1.5 hours. Yield 95%; M.p. 132°–133° C. (from acetone).

EXAMPLE 11–12

The compounds of the following Examples 11 and 12 are obtained by essentially following the procedure of Example 1 but starting from the appropriate 3-aryl-6H-[2]benzopyrano[4,3-c]pyridazin-6-one.

EXAMPLE 11

6-Chloro-3-(4-methoxyphenyl)pyridazino[4,3c]-isoquinoline.

M.p. 224°–227° C. (from toluene)

EXAMPLE 12

6-Chloro-3-(4-chlorophenyl)pyridazino-[4,3-c]isoquinoline. M.p. 228°–230° C. (from diglyme)

EXAMPLES 13–25

The following compounds are prepared in analogy with the procedure of Examples 2–10, starting from the chlorine derivative of Example 11.

EXAMPLE 13

N,N-dimethyl-3-(4-methoxyphenyl)pyridazino[4,3-c]isoquinolin-6-amine.

M.p. 160–162° C. (from acetone)

EXAMPLE 14

1-[[3-(4-methoxyphenyl)pyridazino-[4,3-c]-isoquinolin-6-yl]methylamino]-2-propanol.

M.p. 147°–149° C. (from acetone)

EXAMPLE 15

N,N-bis(2-methoxyethyl)-3-(4-methoxyphenyl)-pyridazino[4,3-c]isoquinolin-6-amine.

M.p. 127°–128° C. (from methanol)

EXAMPLE 16

4-[[3(4-Methoxyphenyl)-pyridazino-[4,3-c]isoquinolin-6-yl]methylamine/butanoic acid ethyl ester.

M.p. 9092° C. (from methyl tert-butylether)

EXAMPLE 17

6-(1-Azetidinyl)-3-(4-methoxyphenyl)pyridazino[4,3-c]isoquinoline.

M.p. 196°–198° C. (from benzene)

EXAMPLE 18

3-(4-Methoxyphenyl)-6-(1-pyrrolidinyl)-piperazino[4,3-c]isoquinoline.

M.p. 176°–177° C. (from ethyl acetate)

EXAMPLE 19

3-(4-Methoxyphenyl)-6-(1-piperidinyl)-pyridazino[4,3-c]isoquinoline.

M.p. 168°–169° C. (from ethyl acetate)

EXAMPLE 20

3-(4-Methoxyphenyl)-6-(4-morpholinyl)-pyridazino[4,3-c]isoquinoline.

M.p. 218°–220° C. (from benzene)

EXAMPLE 21

1-[3-(4-Methoxyphenyl-pyridazino-[4,3-c]isoquinolin-6-yl]-4-piperidincarboxylic acid ethyl ester M.p. 160°–161° C. (from ethanol)

EXAMPLE 22

4-[3-(4-Methoxyphenylpyridazino-[4,3-c]isoquinolin-6-yl-1-piperazincarboxylic acid ethyl ester.

M.p. 199°–200° C. (from acetone)

EXAMPLE 23

1-[3-(4-methoxyphenyl)pyridazino-[4,3-c]isoquinolin-6-yl]-3-piperidincarboxylic acid ethyl ester.

M.p. 181°–183° C. (from water/ethanol)

EXAMPLE 24

6-(2-Methoxyethoxy)-3-(4-methoxyphenyl)-pyridazino[4,3-c]isoquinoline.

M.p. 148°–150° C. (from dioxane)

EXAMPLES 25–30

By essentially following the procedure of Examples 2–10 but starting from the chlorine derivative of Example 12 the following 6-substituted compounds are obtained:

EXAMPLE 25

1-[[3-(4-chlorophenyl)pyridazino[4,3-c]isoquinolin-6-yl]methylamino/-2-propanol.

M.p. 151°–153° C. (from acetone)

EXAMPLE 26

3-(4-Chlorophenyl)-N,N-bis (2-methoxyethyl)pyridazino[4,3-c]isoquinolin-6-amine.

M.p. 123°–125° C. (from methanol)

EXAMPLE 27

3-(4-Chlorophenyl)-6-(1-pyrrolidinyl)pyridazino[4,3-c]isoquinoline.

M.p. 212°–214° C. (from ethyl acetate)

EXAMPLE 28

1-[3-(4-Chlorophenyl)pyridazino-4,3-c]isoquinolin-6-yl]-4-piperidincarboxylic acid ethyl ester.

M.p. 148°–150° C. (from ethanol)

EXAMPLE 29

3-(4-Chlorophenyl)-6-(4-morpholinyl)-pyridazino[4,3-c]isoquinoline.

M.p. 244°–246° C. (from benzene)

EXAMPLE 30

3-(4-Chlorophenyl)-6-(2-methoxyethoxy)pyridazino[4,3-c]isoquinoline.

M.p. 148°–150° C. (from dioxane)

EXAMPLE 31

3-Phenyl-pyridazino[4,3-c]isoquinoline.

(A) A solution of 12.5 g (0.043 mol) of 6-chloro-3-phenyl-pyridazino[4,3-c]isoquinoline (Example 1) in 1.5 L of 2-methoxyethanol is hydrogenated at room temperature and atmospheric pressure in the presence of 2.5 g of 10% palladium on carbon and 1.8 g (0.044 mol) of magnesium oxide. About 1700 ml of hydrogen are absorbed. The mixture is filtered, the solvent evaporated under reduced pressure and the residue recrystallized from isopropanol to give 15 g (74%) of 5,6-dihydro-3-phenyl-pyridazino[4,3-c]isoquinoline.

M.p. 250°–252° C.

(B) To a boiling solution of 3.9 g (0.015 mol) of this dihydro derivative and 14.7 g (0.15 mol) of potassium acetate in 600 ml of ethanol a solution of 3.8 g (0.015 mol) of iodine in 150 ml of ethanol is added dropwise. The reaction mixture is heated at reflux for an additional 2 nours and the solvent is then evaporated under reduced pressure. The residue is taken up with water, filtered and chromatographed on a silica gel column eluted with 1% $CH_3OH$ in $CHCl_3$ to give 2.95 g (76%) of 6-chloro-3-phenyl-pyridazino[4,3-c]isoquinoline.

M.p. 182°–183° C.

EXAMPLE 32

3-Methyl-pyridazino[4,3-c]isoquinoline.

It is prepared by essentially following the procedure of Example 5 but starting from 6-chloro-3-methyl-pyridazino-4,3-c]quisoquinoline instead of 6-chloro-3-phenyl-pyridazino[4,3-c]isoquinoline.

M.p. 150°–152° C. The following compounds of Formula I are prepared by essentially following the procedures of the foregoing Examples:

| R | R₁ | R₂ | R₃ |
|---|----|----|----|
| -⟨C₆H₄⟩-CH₃ | —N(C₂H₅)₂ | H | Cl |
| -⟨C₆H₄⟩-⟨C₆H₄⟩- | —N(CH₂CH₂OCH₃)₂ | H | H |
| -⟨C₆H₄⟩-⟨C₆H₄⟩- | —N(piperazinyl)N—CH₃ | Cl | Cl |
| -⟨C₆H₄⟩-⟨C₆H₄⟩- | —N(pyrrolidinyl) | H | H |

-continued
| R | R₁ | R₂ | R₃ |
|---|---|---|---|
| 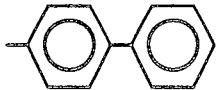 | —N(CH₃)—CH₂CH₂—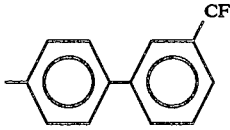 | H | H |
| 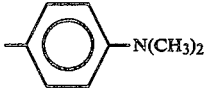 | 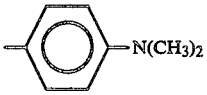 | H | Cl |
|  | 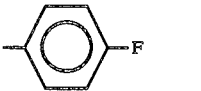 | H | H |
|  | —OCH₂CH₂—O—CO—CH₃ | Cl | Cl |
|  | —N(C₂H₅)₂ | H | Cl |
| 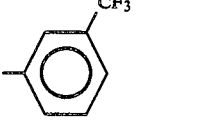 | 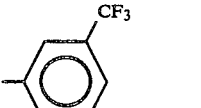 | Cl | Cl |
| 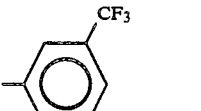 | —N⟩ | Cl | H |

-continued

| R | R1 | R2 | R3 |
|---|---|---|---|
| —⟨C6H4⟩—N(CH2CH2OCH3)2 | —N(2CH3)2 | Cl | H |
| 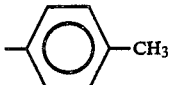 3,5-dimethylphenyl | 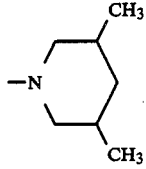 3,5-dimethylpiperidinyl | H | Cl |
| 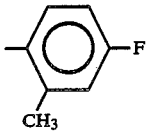 3-methyl-4-fluorophenyl | —N(CH3)CH2CH2—⟨C6H5⟩ | Cl | Cl |
| 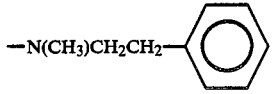 4-CF3-phenyl | 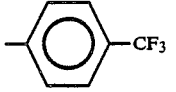 3,3-dimethylazetidinyl | OCH3 | Cl |
| 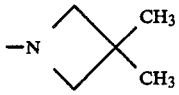 phenyl | —N(CH3)CH2CH2—⟨3,4-dimethoxyphenyl⟩ | OCH3 | H |
|  phenyl | —N(CH3)CH2CH2CH3 | Cl | H |
| 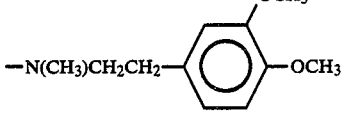 phenyl | —N(CH3)CH2CH—CH3<br>            \|<br>           CH3 | H | Cl |
|  phenyl | —OCH2CH2OH | H | H |
|  phenyl |  piperazinyl | Cl | H |
|  phenyl |  piperazinyl | H | H |
|  phenyl | 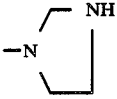 morpholinyl | H | H |
|  phenyl | —N(CH2CH2OCH3)2 | H | Cl |

I claim:

1. Pyridazino[4,3-c]isoquinolines of Formula I

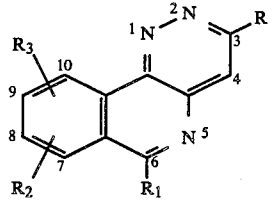

wherein R represents methyl, phenyl or substituted phenyl, wherein the phenyl ring is substituted with from 1 to 3 substituents selected from $(C_1-C_4)$alkyl, $(C_1-C_4)$alkoxy, halogen, phenyl and trifluoromethyl; $R_1$ represents hydrogen, chloro, a group of Formula $-NR_4R_5$ wherein $R_4$ and $R_5$, each independently, represent hydrogen, $(C_1-C_4)$alkyl, $(C_2-C_4)$alkenyl, $(C_2-C_5)$alkanoyloxymethyl, $(C_1-C_4)$alkoxycarbonyl, $(C_1-C_4)$alkyl substituted with one or two groups independently selected from hydroxy, $(C_1-C_4)$alkoxy, halogen, carboxy, cyano and aminocarbonyl, phenyl$(C_1-C_4)$alkyl or substituted phenyl-$(C_1-C_4)$alkyl wherein the alkyl portion may be substituted with one or two groups selected from hydroxy, $(C_1-C_4)$alkoxy, halogen, carboxy, $(C_1-C_4)$alkoxycarbonyl, and $(C_2-C_4)$alkanoyloxymethyl, and the phenyl portion may be substituted as defined, above, or $R_4$ and $R_5$ taken together with the adjacent nitrogen atom represent a saturated 4, 5, 6, or 7-membered heterocyclic ring which may contain a further heteroatom selected from oxygen and sulfur and optionally bear one or two substituents independently selected from $(C_1-C_4)$alkyl, phenyl, hydroxy, and carbo$(C_1-C_4)$alkoxy, or $R_1$ represents an alkoxy or cycloalkoxy group of Formula $-OR_6$ wherein $R_6$ stands for a $(C_1-C_6)$alkyl substituted with one or two groups independently selected from hydroxy, amino, mono- or di-$(C_1-C_4)$alkylamino, $(C_1-C_4)$alkoxy, halogen, oxo, carboxy, aminocarbonyl, mono- or di-$(C_1-C_4)$-alkylaminocarbonyl, and $(C_1-C_4)$alkoxycarbonyl, or $R_6$ is a $(C_5-C_8)$cycloalkyl group optionally substituted with at least one substituent selected from hydroxy and $(C_1-C_4)$alkoxy, $R_2$ and $R_3$ independently represent hydrogen, halogen, $(C_1-C_4)$alkyl or $(C_1-C_4)$alkoxy; and the pharmaceutically acceptable acid addition salts thereof.

2. A compound according to claim 1 wherein R is methyl, phenyl or substituted phenyl, $R_1$ is a group of Formula $-NR_4R_5$ wherein $R_4$ and $R_5$ independently represent hydrogen, $(C_1-C_4)$alkyl, and $(C_1-C_4)$ alkyl substituted with one group selected from $(C_1-C_4)$alkoxy and hydroxy or $R_4$ and $R_5$ taken together with the adjacent nitrogen atom represent a saturated heterocyclic group selected from azetidinyl, pyrrolydinyl, piperidinyl, and morpholinyl, $R_2$ and $R_3$ independently represent hydrogen or halogen atoms and the pharmaceutically acceptable acid addition salts thereof.

3. A compound according to claim 1 which is 3-phenyl-6-(1-pyrrolidinyl)pyridazino-[4,3]isoquinoline.

4. A 3-substituted pyridazino[4,3-c]pyridine of the following Formula III

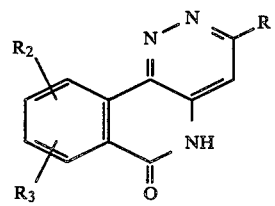

wherein $R_1$, $R_2$ and $R_3$ are as defined in claim 1.

5. An anti-anxiety pharmaceutical composition comprising an antianxiety effective amount of a compound of claim 1 as the active ingredient in admixture with a pharmaceutically acceptable vehicle.

6. An anti-anxiety pharmaceutical composition comprising an anti-anxiety effective amount of from 25 mg to 250 mg of a compound of claim 1 as the active ingredient in admixture with a pharmaceutically acceptable carrier.

7. A method of treating anxiety in a patient in need thereof which comprises administering to the patient an anti-anxiety effective amount of a compound of claim 1.

* * * * *

UNITED STATES PATENT AND TRADEMARK OFFICE
CERTIFICATE OF CORRECTION

PATENT NO. : 4,716,159

DATED : December 29, 1987

INVENTOR(S) : Emilio Toja

It is certified that error appears in the above-identified patent and that said Letters Patent are hereby corrected as shown below:

At column 2, line 27, the patent reads "propionylcxvmethyl" and should read --propionyloxymethyl--.

At column 5, line 59, the patent reads "Möler" and should read --Möhler--.

At column 7, line 26, the patent reads "text compound" and should read --test compound--.

At column 8, line 66, the patent reads "-4,3-c]" and should read -- -[4,3-c] --.

At column 9, line 1, the patent reads "3-](2,3-" and should read -- 3-[(2,3- --.

At column 9, line 36, the patent reads "-[4,3-c" and should read -- [4,3-c]- --.

At column 9, line 41, the patent reads "imin-o/propanoic" and should read --imino]propanoic--.

At column 9, line 43, the patent reads "pyridazinyl-]" and should read -- pyridazinyl] --.

At column 9, line 49, the patent reads "3-(2,3-" and should read -- 3-[(2,3- --.

At column 9, line 59, the patent reads "-]4,3-c]" and should read -- -[4,3-c] --.

At column 10, line 21, the patent reads "6-chloro 3-" and should read -- 6-chloro-3- --.

At column 11, line 51, the patent reads "[4,3isoquinoline." and should read -- [4,3-c]isoquinoline --.

At column 11, line 65, the patent reads "[4,3c]" and should read -- [4,3-c] --.

At column 12, line 30, the patent reads "methylamine/butanoic" and should read --methylamine]butanoic--.

UNITED STATES PATENT AND TRADEMARK OFFICE
CERTIFICATE OF CORRECTION

PATENT NO. : 4,716,159

DATED : December 29, 1987

INVENTOR(S) : Emilio Toja

It is certified that error appears in the above-identified patent and that said Letters Patent are hereby corrected as shown below:

At column 12, line 66, the patent reads "-6-yl-1-" and should read -- -6-yl]-1- --.

At column 13, line 22, the patent reads "methylamino/-2-" and should read -- methylamino]-2- --.

At column 13, line 38, the patent reads "-4,3-c]" and should read -- -[4,3-c] --.

At column 14, line 26, the patent reads "2 nours" and should read --2 hours--.

At column 14, line 37, the patent reads "pyridazino-4,3-c]quisoquinoline" and should read -- pyridazino[4,3-c]isoquinoline--.

At column 20, line 16, claim 3, the patent reads "-[4,3]isoquinoline" and should read -- -[4,3-c]isoquinoline --

Signed and Sealed this

Thirty-first Day of May, 1988

Attest:

DONALD J. QUIGG

Attesting Officer

Commissioner of Patents and Trademarks